United States Patent [19]

Bahrmann et al.

[11] Patent Number: 5,773,667
[45] Date of Patent: Jun. 30, 1998

[54] PROCESS FOR PREPARING ALDEHYES

[75] Inventors: Helmut Bahrmann, Hamminkeln; Thomas Muller, Dinslaken; Rainer Lukas, Essen, all of Germany

[73] Assignee: Hoechst Aktiengesellschaft, Germany

[21] Appl. No.: 856,212

[22] Filed: May 14, 1997

[30] Foreign Application Priority Data

May 15, 1996 [DE] Germany ............... 196 19 527.6
Aug. 13, 1996 [DE] Germany ............... 196 32 600.1

[51] Int. Cl.$^6$ ................................... C07C 45/50
[52] U.S. Cl. ................ 568/454; 568/451; 210/644; 210/651
[58] Field of Search ................. 568/451, 454; 210/644, 651

[56] References Cited

U.S. PATENT DOCUMENTS

Re. 35,292  7/1996  Bahrmann et al. ............ 210/644

Primary Examiner—Gary Geist
Assistant Examiner—Sreeni Padmanabhan
Attorney, Agent, or Firm—Bierman, Muserlian and Lucas

[57] ABSTRACT

A process for preparing aldehydes comprising hydroformylating olefinically unsaturated compounds with hydrogen and carbon monoxide in a homogeneous phase in the presence of a catalyst system comprising rhodium complex compounds and aromatic phosphines in a molar excess and separating off the catalyst system from the hydroformylation reaction mixture by pressure filtration on a semipermeable membrane of an aromatic polyamide by carrying out the hydroformylation at a pH of 2.5 to 4.3 using a molar ratio of phosphine:rhodium of at least 60 and at a rhodium concentration of at least 10 ppm by weight, based on the olefinically unsaturated compound used, and using, as aromatic phosphines, special alkylammonium and/or arylammonium salts of sulfonated or carboxylated triarylphosphines which process leads to excellent activities and selectivities in the hydroformylation step itself and also to high retention values in the membrane filtration step.

25 Claims, No Drawings

PROCESS FOR PREPARING ALDEHYES

FIELD OF THE INVENTION

A process for preparing aldehydes by reaction of olefinically unsaturated compounds with hydrogen and carbon monoxide in homogeneous phase and in the presence of a catalyst system comprising rhodium complex compounds and aromatic phosphines in a molar excess, and separating off the catalyst system from the reaction product by membrane filtration.

STATE OF THE ART

The hydroformylation of olefins, carried out industrially to a great extent, is increasingly being performed in the presence of catalyst systems based on rhodium complex compounds which comprise tertiary phosphines or phosphites as ligands. Since the ligands are generally present in excess, the catalyst system comprises the organometallic complex compound and excess free ligand. In accordance with the solubility of these catalyst systems in organic media, the hydroformylation is performed in homogeneous phase.

To separate off the reaction products and recover the catalyst system homogeneously dissolved in the reaction product, the reaction product is generally distilled off from the reaction mixture. However, owing to the thermal sensitivity of the aldehydes formed, this is only possible in the hydroformylation of lower olefins having up to about 8 carbon atoms in the molecule. In the hydroformylation of long-chain olefins or olefinic compounds having functional groups, thermally sensitive products, or products having a high boiling point, are formed, which can no longer be satisfactorily separated off from the catalyst by distillation. The thermal stress of the distillation material leads, owing to thick oil formation, to considerable losses of valuable product and, owing to decomposition of the complex compounds, to losses of catalyst. This critically decreases the economic attractiveness of the process.

To avoid separating off the catalyst system in a thermal manner, various process alternatives have been developed. EP-A-0 216 375 discloses a process for preparing aldehydes by reaction of olefins with hydrogen and carbon monoxide in homogeneous phase in the presence of a catalyst system comprising rhodium and aromatic phosphines in molar excess, in which the aromatic phosphines used are salts of sulfonated or carboxylated triarylphosphines which are soluble in organic media and insoluble in water. The cations of these salts are ammonium ions of the formulae $(NR_2H_2)^+$ and or $(NR_3H)^+$, where R is alkyl of 4 to 12 carbon atoms or aryl or cycloalkyl of 6 to 12 carbon atoms.

To separate off the catalyst system from the reaction product, in this case, the hydroformylation mixture is first treated with a base, e.g. alkali metal hydroxide or alkaline earth metal hydroxide solutions. In this case, the corresponding secondary or tertiary amines are released from the $(NR_2H_2)^+$ or $(NR_3H)^+$ salts, and, simultaneously, a water-soluble alkali metal salt or alkaline earth metal salt of the sulfonated or carboxylated triarylphosphine is formed, which thus passes into the aqueous phase and, together with the complex of phosphorous-bound rhodium, can be separated from the organic phase containing the hydroformylation product via an extraction.

EP-A-0 374 615 further discloses that organometallic complex compounds which contain phosphorus(III) compounds as ligands, after their use as catalysts for the hydroformylation of olefins in homogeneous phase, can be separated from the hydroformylation products by membrane filtration. Using selective semi-permeable polyaramid separation membranes, it is possible to separate and recover the organometallic complex compounds undamaged, i.e. without degradation of the catalytically active metal compound. Either a pressure difference (pressure filtration) or a concentration difference (dialysis) can serve as motive force for the separation process in this case.

The rhodium complex compounds which are to be successfully separated are mentioned in EP-A-0 374 615 as $HRhCO[P(C_6H_5)_3]_3$, $RhCl[(P(C_6H_5)_3]_3$ and those compounds which contain, as ligands, alkylammonium or arylammonium salts of sulfonated or carboxylated triarylphosphines of the formula

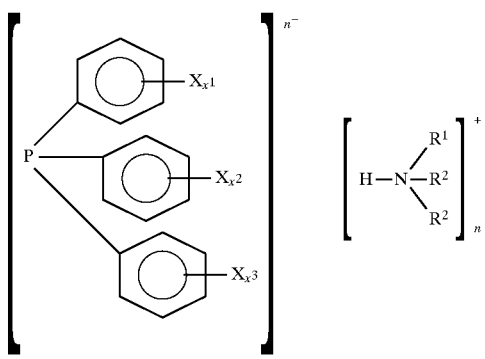

wherein X is sulfonate $(SO_3^-)$ or carboxylate $(COO^-)$, $x^1$, $x^2$ and $X^3$ are 0 or 1, $R^1$ and $R^2$ are individually alkyl of 4 to 12 carbon atoms, aryl of 6 to 12 carbon atoms or cycloalkyl of 6 to 12 carbon atoms and $R^1$ can additionally also be hydrogen.

In the two-stage membrane separation of a catalyst comprising rhodium and the triisooctylammonium salt of tris(m-sulfo-phenyl)phosphine from the crude product of the dicyclopentadiene hydroformylation according to EP-A-0 374 615, 99.5% of the rhodium and 94.4% of the phosphorus(III) compound are retained. 5.6% of the phosphorus(III) compound thus remains in the organic hydroformylation product and can be removed therefrom only by complex measures, such as a complicated distillation with relatively large product losses. The flow rate in the final steady state of membrane filtration is only 5 or 10 $l/m^2$ h in the first or second membrane filtration stage, respectively.

OBJECTS OF THE INVENTION

It is an object of the invention to provide a process for the hydroformylation of olefinically unsaturated compounds in homogeneous phase which gives high activities and selectivities and simultaneously enables improved separation of the entire catalyst system.

This and other objects and advantages of the processes of the invention will become obvious from the following detailed description.

THE INVENTION

The novel process of the invention for preparing aldehydes comprises hydroformylating olefinically unsaturated compounds with hydrogen and carbon monoxide in homogeneous phase in the presence of a catalyst system comprising rhodium complex compounds and aromatic phosphines in a molar excess and separating off the catalyst system from the hydroformylation reaction mixture by pressure filtration on a semipermeable membrane of an aromatic polyamide, the hydroformylation being effected at a pH of 2.5 to 4.3 using a molar ratio of phosphine:rhodium of at least 60 and at a rhodium concentration of at least 10 ppm by weight, based on the olefinically unsaturated compound used, and using, as aromatic phosphines, alkylammonium and/or arylammonium salts of sulfonated or carboxylated triarylphosphines of the formula

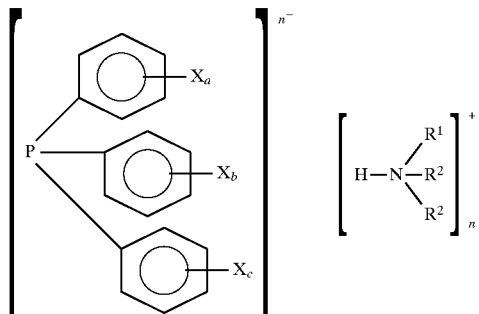

wherein X is sulfonate ($SO_3^-$) or carboxylate ($COO^-$), a, b and c are individually 0 or 1, with at least one of the parameters a, b or c being equal to 1, n is equal to 1, 2 or 3, $R^1$ and $R^2$ are individually alkyl of 8 to 13 carbon atoms or aryl of 6 to 10 carbon atoms or cycloalkyl of 6 to 10 carbon atoms, and $R^1$ can also be hydrogen, and the total of the carbon atoms in $R^1$ and $R^2$ must be at least 30.

The aromatic phosphines of formula I are present as ammonium carboxylates or ammonium sulfonates having a singly to triply charged phosphine anion and the corresponding number of ammonium cations as counter ions. They are insoluble in water or soluble in water only to an extremely slight extent. In organic solvents, in contrast, they have good to very good solubility and are therefore particularly suitable for use in organic phase.

In formula I, X is carboxylate or sulfonate, preferably sulfonate. a, b and c are individually 0 or 1, where at least one of a, b or c must be 1. Preferably, a, b and c are equal to 1.

$R^1$ and $R^2$ are individually alkyl of 8 to 30 carbon atoms, preferably alkyl of 12 to 22 carbon atoms, or $C_6$–$C_{10}$-aryl or cycloalkyl of 6 to 10 carbon atoms, preferably phenyl or cyclohexyl, where $R^1$ can also be hydrogen.

Thus, the ammonium cations $[H-NR^1R^2R^2]^+$ are derived from secondary or tertiary amines and contain at least 30 and at most 90, preferably 32–70, and more preferably 36–54, carbon atoms in $R^1$ and $R^2$. Preferably, the ammonium cations are the distearylammonium ion, the tricetylammonium ion or the tri-n-octadecylammonium ion.

To prepare the ammonium salts of the sulfonated triphenylphosphine, triphenylphosphine is first, in accordance with DE-26 27 354, sulfonated by reaction with excess sulfotrioxide in the form of oleum, the sulfonation mixture is diluted with water and then the water-insoluble amine $NR^1R^2R^2$ dissolved in a water-insoluble organic solvent is added. In this case, the corresponding ammonium salts of the sulfonated triphenylphosphine form, which can be separated off as organic phase.

The catalyst system of rhodium or a rhodium compound and the phosphine compound of formula I is formed either in a step upstream of the hydroformylation, the so-called preforming, or else, particularly in the case of a continuous procedure, in situ during the hydroformylation reaction.

The preforming upstream of the hydroformylation is preferably carried out in the same reactor in which the hydroformylation also subsequently takes place, but it can also be carried out in a separate reaction vessel.

To prepare the catalyst system by preforming, the rhodium component (rhodium or a rhodium compound) is brought together with the phosphine compound of formula I either in the hydroformylation reactor or in a separate apparatus. In this case, both the rhodium or the rhodium compound and the phosphine compound of formula I are used as a solution in an organic solvent or, in the case of elemental rhodium, in a suspension.

Suitable solvents are, in this case, organic solvents which are inert under the conditions of the subsequent hydroformylation such as toluene, ortho-xylene, meta-xylene, para-xylene, mixtures of isomeric xylenes, 2-ethylhexanol, ethylbenzene, mesitylene, mixtures of these compounds, or aliphatic hydrocarbons. Preferably, o-xylene or toluene is used.

The rhodium/phosphine mixture is then impinged with a mixture of carbon monoxide and hydrogen and reacted at a carbon monoxide/hydrogen pressure of 0.5 to 27 MPa at temperatures of 80° to 150° C. for at least 1 hour, with formation of water-insoluble rhodium complex compounds which are soluble in organic media and which contain the phosphine as ligands. Together with the phosphine excess dissolved in the organic solvent, they form the catalyst system. The catalyst system solution can then, if it is prepared in a separate apparatus, be transferred to the hydroformylation reactor and admixed with the olefin to be hydroformylated.

If the catalyst system is to be prepared in situ during the hydroformylation reaction, the above-described components, rhodium or rhodium compound and phosphine, are introduced into the hydroformylation reactor simultaneously with the olefin.

Rhodium is used either as metal or as compound. In metallic form, it is used in the form of finely divided particles or deposited in a thin layer on a support such as activated carbon, calcium carbonate, aluminum silicate or alumina. Rhodium compounds which are suitable are those substances which are soluble or can be suspended in organic solvents or are soluble or can be suspended therein under reaction conditions. Suitable substances are the various rhodium oxides, salts of inorganic hydrogen acids or oxo acids, and salts of aliphatic monocarboxylic or polycarboxylic acids. Examples of rhodium salts are rhodium nitrate, rhodium sulfate, rhodium acetate, rhodium 2-ethylhexanoate, rhodium malonate. Rhodium halogen compounds, due to the reduced activity of the resulting complexes, and due to the corrosive behavior of the halide ions, in contrast, are less suitable. Furthermore, rhodium carbonyl compounds, such as $Rh_4(CO)_{12}$ or $Rh_6(CO)_{16}$, or complex rhodium salts, e.g. cyclooctadienylrhodium compounds, can be used. Preference is given to rhodium oxide, with particular preference being given to rhodium acetate and rhodium 2-ethyl-hexanoate.

It is not necessary to use the phosphine ligands of formula I in the catalyst system as uniform compounds. It is also possible to use, e.g. differing sulfonation stages of the phosphines and/or sulfonate mixtures having different ammonium cations.

It has proven to be useful in the formation and use of catalyst systems not to use rhodium and the aromatic phosphines of formula I in a stoichiometric ratio, that is in accordance with the chemical composition of the rhodium complex compound which forms, but to use the aromatic phosphines in excess. It is essential here that at least 60 mols of phosphine are used per mol of rhodium. Preference is given to a molar ratio of rhodium to aromatic phosphine of 1:(60–120). Particularly preferable, a ratio of 1:(70–110) is used, and, more preferably, a ratio of 1:(80–100) is used.

Furthermore, it has proved to be essential that the rhodium concentration in the hydroformylation, based on the olefinically unsaturated compound, is at least 10 ppm by weight, preferably at least 20 ppm by weight, and more preferably 60 to 150 ppm by weight.

In the process of the invention, olefinically unsaturated compounds of 2 to 30 carbon atoms which can have one or more double bonds are reacted. Suitable substances are substituted or unsubstituted alkenes of 6 to 30 carbon atoms, substituted or unsubstituted dienes of 4 to 10 carbon atoms, substituted or unsubstituted cycloalkenes or dicycloalkenes of 5 to 12 carbon atoms in the ring system, esters of an unsaturated carboxylic acid of 3 to 20 carbon atoms and of an aliphatic alcohol of 1 to 18 carbon atoms, esters of a saturated carboxylic acid of 2 to 20 carbon atoms and of an unsaturated alcohol of 2 to 18 carbon atoms, unsaturated alcohols or ethers each of 3 to 20 carbon atoms or araliphatic olefins of 8 to 20 carbon atoms.

The substituted or unsubstituted alkenes of 6 to 30 carbon atoms can be linear or branched alkenes having a terminal or internal position of the double bond. Preference is given to linear olefins of 6 to 18 carbon atoms such as n-hex-1-ene, n-hept-1-ene, n-oct-1-ene, n-non-1-ene, n-dec-1-ene, n-undec-1-ene, n-dodec-1-ene, n-octadec-1-ene and acyclic terpenes. Suitable substances are also branched alkenes such as diisobutylene (2,4,4-trimethylpent-1-ene), tripropylene, tetrapropylene and dimersol (dibutylene).

Preferred examples of unsubstituted dienes of 4 to 10 carbon atoms are 1,3-butadiene, 1,5-hexadiene and 1,9-decadiene.

Examples of substituted and unsubstituted cycloalkenes or dicycloalkenes of 5 to 12 carbon atoms in the ring system are cyclohexene, cyclooctene, cyclooctadiene, dicyclopentadiene and cyclic terpenes such as limonene, pinene, camphorene and bisabolene. Preference is given to dicyclopentadiene.

An example of araliphatic olefins of 8 to 20 carbon atoms is styrene.

Examples of esters of an unsaturated carboxylic acid of 3 to 20 carbon atoms and an aliphatic alcohol of 1 to 18 carbon atoms which may be mentioned are acrylic esters and methacrylic esters of 1 to 18 carbon atoms in the alcohol component.

The esters of a saturated carboxylic acid of 2–20 carbon atoms and an unsaturated alcohol of 2–18 carbon atoms include vinyl esters and allyl esters of 2–20 carbon atoms in the carboxylic acid component, for example vinyl acetate.

The unsaturated alcohols and ethers include, for example, allyl alcohols and vinyl ethers.

The olefin is reacted with carbon monoxide and hydrogen at a temperature of 100° to 140° C., preferably 120° to 130° C. and at a pressure of 0.5 to 27 MPa, preferably 20 to 25 MPa. The composition of the synthesis gas, i.e. the volumetric ratio of carbon monoxide and hydrogen, can extend over broad ranges and can be varied, e.g. between 1:10 and 10:1. Generally, gas mixtures are used in which the volumetric ratio of carbon monoxide and hydrogen is about 1:1 or deviates only slightly from this value.

Furthermore, it is of great importance that the hydroformylation is carried out at a pH of 2.5 to 4.3, preferably 3.0 to 4.0, preferably 3.5. In the course of the hydroformylation, the pH can continuously fall owing to dissociation of the ammonium salt of the sulfonated or carboxylated triphenylphosphine into free amine and the corresponding sulfonic acid or carboxylic acid form of the triphenylphosphine. To establish the above-mentioned pH, if required, free amine $NR^1R^2R^2$, or a metal hydroxide is added in appropriate amounts.

Preferably, the process of the invention is carried out in the presence of an organic solvent which is inert under the hydroformylation conditions and, in addition, does not attack the membrane in the membrane filtration stage. Suitable solvents are aromatic hydrocarbons, e.g. toluene, ortho-xylene, meta-xylene, para-xylene, mixtures of isomeric xylenes, ethylbenzene, mesitylene, mixtures of these compounds, or aliphatic hydrocarbons. However, more polar solvents, such as acetophenone, tetrahydrofuran, sulfinol, glycols or polyglycols, can also be useful.

However, the process of the invention can also be carried out without the addition of an organic solvent, the olefinic starting compound and the hydroformylation product formed acting as the solvent in this case. However, on account of the usually higher viscosity of a reaction mixture of this type, only relatively low flow rates are then achieved in the membrane filtration.

The aldehydes are prepared by reacting the reaction partners present in liquid and gaseous phase in conventional reactors, and can be prepared either continuously or batchwise.

After hydroformylation is completed, the reaction mixture is generally cooled, freed from gaseous constituents by expansion and blanketed with an inert gas such as nitrogen or with a synthesis gas mixture of CO and $H_2$. The mixture is then separated by means of membrane filtration. However, the reaction mixture can also be fed to the membrane separation without cooling.

In the hydroformylation reaction mixture used for the membrane filtration, the concentration of the aromatic phosphines of formula I present in excess is 2.5 to 25, preferably 5 to 15, % by weight, based on the total reaction mixture used for the membrane filtration.

The concentration of the rhodium complex compounds in the hydroformylation reaction mixture used for the membrane filtration is 2 to 400 ppm by weight, preferably 10 to 300 ppm by weight, more preferably 50 to 150 ppm by weight, based on the total reaction mixture used for the membrane filtration.

The membrane filtration is performed on a semipermeable membrane of an aromatic polyamide at a pressure of 0.1–15, preferably 0.5–5, in particular 1–2, MPa. The membrane filtration can be carried out in a single stage or in multiple stages. Preferably it is carried out in multiple stages, especially in two stages. It can be carried out either using parallel or series-connected separation stages. Preference is given to connection in series, in which the retentate is separated in each stage and the permeate solution is passed to the next separation stage. A series connection in this manner permits a particularly effective utilization of the existing system pressure, i.e. the operating pressure in the preceding process step.

Particularly high separation efficiencies are achieved if the total amount of retentate is 8 to 90, preferably 10 to 70, more preferably 15 to 50, and, in particular, 20 to 40% based on the reaction mixture used for the membrane filtration, and the concentration of the separated aromatic phosphines of formula I in the membrane filtration retentate is at least three times as high as in the hydroformylation reaction mixture used for the membrane filtration.

In the two-stage membrane filtration, it has, further, proved to be useful that the ratio of the amount of retentate of the 1st filtration stage to the amount of retentate of the 2nd filtration stage is about 1:1.

A further increase in the separation efficiency of the membrane when the above-described process variant is used is achieved by increasing the overflow of the membrane using a circulation pump. The linear flow velocity over the membrane is usually in the range of 0.1 to 10 m/sec, preferably 0.5 to 2.5 m/sec.

The separation stage retentates containing the catalyst system can be combined and recycled back to the hydroformylation, optionally with supplementary addition of the rhodium and/or the rhodium complex compounds and of the aromatic phosphines of formula I. These supplementary amounts can, in the case of a two-stage membrane filtration procedure, also even be added to the permeate of the 1st stage prior to its feed to the 2nd membrane filtration stage. In this manner, an improved separation result is achieved and multiple reuse of the catalyst system in the hydroformylation is enabled, without significant losses with regard to activity and selectivity of the catalyst system occurring.

If the process of the invention is carried out in the presence of a solvent, a particularly high total efficiency both of the hydroformylation step and of the membrane separation step can be achieved if the hydroformylation stage is operated with little solvent to achieve the highest possible conversion rate, but the membrane stage is operated with much solvent to decrease the viscosity. In the hydroformylation stage, a solvent concentration of 5 to 25% by weight, preferably 7 to 13% by weight, based on the total hydroformylation reaction mixture, has proved to be useful. In contrast, in the membrane filtration step, 30 to 70% by weight, particularly 40 to 60% by weight, of solvent, based on the total reaction mixture used for the membrane filtration, is preferred. This higher solvent concentration in the reaction mixture used for the membrane filtration is achieved by separating by distillation the organic solvent from the combined permeates of the membrane filtration stages and recycling it upstream of the membrane filtration. There, it is added back to the hydroformylation reaction mixture to be separated and this attains the appropriate dilution which serves to achieve high flow rates.

The membranes used in the invention consist of an aromatic polyamide, also termed polyaramid. The polyaramids are obtained by polycondensation of aromatic dicarboxylic acids or dicarboxylic acid derivatives and aromatic diamines in a dipolar aprotic solvent. Suitable carboxylic acid components are terephthalic acid, 4,4'-biphenyldicarboxylic acid, 4,4'-diphenyl ether dicarboxylic acid, 4,4'-diphenyl sulfone dicarboxylic acid or 2,6-naphthalenedicarboxylic acid. Suitable diamine components are p-phenylenediamine, 3,3'-dimethoxybenzidine, 3,3'-dichlorobenzidine, 3,3'-dimethylbenzidine, 4,4'-diaminodiphenylmethane, 2,2-bis-(4-aminophenyl)propane or 1,4-bis(4-aminophenoxy)benzene.

Particular importance is attached to membranes of those polyaramids which, in addition to a carboxylic acid component, contain different diamines as monomers. Thus, polyaramids have proved to be useful which are made up of terephthalic acid, p-phenylenediamine, 1,4-bis(4-aminophenoxy)benzene and 3,3'-dimethylbenzidine. The amines can be randomly distributed in the polymers, but the polyamides can also have the structure of block copolymers.

The mean molecular weight of the polyaramids can extend over a broad range and usually, it is 5,000 to 200,000. Preference is given to polyaramids having a molar mass of 10,000 to 50,000.

To produce the membranes of the invention, a process has proved to be useful which is described in German Patent Application P 38 02 030. The membranes disclosed here consist of a copolyamide which is made up of three different diamines and one dicarboxylic acid. A solution of this copolyamide in an aprotic polar solvent of the amide type, e.g. N-methyl-2-pyrrolidone, is spread out as a liquid layer on a planar support. This liquid layer is introduced into the precipitant liquid, particularly water, which is miscible with the solvent of the solution, but the polymer precipitates out as membrane. The precipitant liquid is allowed to act on the precipitated membrane until the solvent is completely replaced by the precipitant liquid. If necessary, the membrane can be further subjected to a heat treatment. The membrane is then dried, optionally after a prior treatment with glycerol.

The membranes produced by the above-described process are integrally asymmetric and are known in principle to those skilled in the art. The membranes have a very thin separation layer, whose thickness is 0.05 to 5$\mu$, and a porous support structure. The thickness of the membrane consisting of separation layer and support structure can be 10 to 400$\mu$, and is preferably in the range from 50 to 200$\mu$.

The shape of the membrane can be selected as desired. It can be constructed as a disk, and, particularly as a hollow fiber or capillary, but can also have any other shape suitable for the contemplated use. The critical factor is achieving a stability as high as possible and, furthermore, the highest possible surface area per unit volume to achieve a satisfactory throughput.

It is advisable to pretreat the membrane prior to use. In the simplest case, it is immersed into the solution to be separated. However, other conditioning processes are also possible. The membrane impregnated with glycerol for storage purposes is first washed with water and then left for 10 minutes in water at 80°–100° C. The water is then replaced, e.g. by i-propanol, by layering the membrane in i-propanol and repeatedly replacing the alcohol. The i-propanol is then in the same manner replaced by the hydroformylation reaction mixture in which the rhodium complex compounds to be separated off and the aromatic phosphines of formula I are dissolved.

To achieve an optimum separation efficiency, it has further proved to be useful to let the membrane run in under operating conditions for a certain time, i.e. to carry out the membrane filtration using the hydroformylation reaction mixture, but to recombine the resulting retentates and permeates and to recycle them to the hydroformylation reaction mixture upstream of the membrane filtration. As a result of this so-called pressure conditioning, further membrane pores close, as a result of which the separation efficiency of the membrane increases. The type and method of the membrane conditioning determine the operating conditions to be maintained in the process of the invention.

The process of the invention is distinguished by the combination of various special hydroformylation conditions and the use of aromatic phosphine ligands with particular ammonium cations. If the previously mentioned values or ranges of values for the rhodium concentration, based on the olefin used, the phosphine:rhodium ratio and the pH are maintained, and phosphine ligands of formula I are used, not only are excellent selectivities and activities obtained in the hydroformylation step, but also excellent retention values are obtained in the subsequent membrane filtration. In a single-stage membrane filtration, 95–98% of the rhodium and at least 90% of the ligand are retained. In a two-stage procedure, 99–99.5% of the rhodium and at least 97%, in many cases even more than 98%, of the ligand are recovered. In this case, simultaneous compliance with said ranges of values for the parameters and also choice of the correct phosphine ligand are of importance.

If only one of the parameters or the ligand departs from said ranges of values or formula I, this causes adverse consequences to be observed either in the hydroformylation or in the membrane filtration or in both steps. If the ammonium salts are derived, e.g. from tertiary amines having an excessively high number of carbon atoms in $R^1$ and $R^2$, although excellent retention rates for ligand and amine are achieved due to the high stearic requirement of the amine, due to the high molecular weight of the amine, establishing the P:Rh ratio of at least 60 required for good hydroformylation results leads to the presence of an extremely large amount of ligand in the reactor. As a result, the reactor volume available for the remaining reactants, in particular the olefin, decreases accordingly. This is an effect which leads to lower product throughputs in the hydroformylation step and thus to increased processing costs, which has the consequence of a decreased economic attractiveness of the process.

If, in contrast, an amine having an insufficient number of carbon atoms is used, e.g. triisooctylamine, although excellent selectivities are achieved in the hydroformylation, the retention rates in the membrane filtration are considerably lower. If the specified pH range is not maintained, there is likewise an impairment of the hydroformylation reaction in the form of a reduced selectivity. If the process of the invention is carried out in the presence of a solvent, it is essential to use a reaction mixture having a solvent concentration of 30–70% by weight in the membrane filtration. If less solvent is used, the flow rates decrease, so that correspondingly larger membrane areas have to be used to achieve sufficient throughputs. However, if the same solvent concentration of 30–70% by weight is also used in the hydroformylation stage, the conversion rate and the productivity of the process decrease. Here, it is therefore advantageous to keep a solvent concentration of only 5–25% by weight in the reaction mixture.

In the following examples, there are described several preferred embodiments to illustrate the invention. However, it is to be understood that the invention is not intended to be limited to the specific embodiments.

EXAMPLES

Firstly, the production of a membrane of a type which can be used in the process of the invention is described.

Membrane Production

The polyaramid was prepared by condensation of
97–99 mol % of terephthaloyl dichloride
25 mol % of p-phenylenediamine
25 mol % of 1,4-bis(4-aminophenoxy)benzene
50 mol % of 3,3'-dimethylbenzidine
in N-methylpyrrolidone as solvent. Terephthaloyl dichloride was used in an amount so that the polyaramid had a Staudinger index of 200 to 300 ml/g. The amount of solvent was such that a solution containing about 7% by weight of polycondensate was formed. After the condensation had been carried out, the hydrogen chloride loosely bound to the solvent was neutralized by addition of 100 mol % CaO. 5% by weight (based on the polymer solution) of anhydrous calcium chloride was then dissolved, with stirring, in the reaction mixture. The solution was gently heated, filtered and degassed and was used directly for membrane production.

It was possible to produce the membrane support-free or on a polyester fleece as support. Production of a support-free membrane is described below. The slightly heated polyaramid solution was drawn out with a blade onto a glass plate to form a uniform film of about $150\mu$ and immersed in a waterbath of 2° C. After about 20 minutes, the membrane was pulled off from the glass plate and was placed for 5 minutes in water at 100° C. The membrane was then placed in i-propanol, to replace the pore liquid water with alcohol. The membrane was then washed with toluene, and after this treatment, it was suitable for carrying out the separations. In all operations, care had to be taken to ensure that the membrane did not dry out.

Examples 1–7. Comparison Experiment 1

Hydroformylation of dicyclopentadiene (DCP) using catalyst systems which comprise rhodium and various ammonium salts of triphenylphosphinetrisulfonate (TPPTS):

a) Preparation of the distearylammonium salt of TPPTS 253 g of an Na-TPPTS solution were introduced into a stirred flask under nitrogen and heated to 65° C. and a solution of 250.3 g of distearylamine in 595 g of toluene was then added. In the course of 60 minutes, 90 ml of 20% strength sulfuric acid were added with stirring until a pH of 2.6 was attained and the mixture was allowed to react further for 2.5 hours. 170 g of isopropanol were added for improved phase separation. After 15 minutes, 1037.5 g of an organic phase which contained the distearylammonium salt of TPPTS containing 0.33 mol of TPPTs per mol of amine were separated.

Other ammonium salts of TPPTS (Examples 2–7 and Comparison Experiment 1) were prepared in a similar manner to the above instructions.

b) Batchwise hydroformylation of dicyclopentadiene

A 2.15 liter stirred autoclave was flushed with nitrogen and 212.8 g of the particular ligand solution from a) and 0.29 mmol of rhodium in the form of a 2-ethylhexanoate salt were dissolved (60 ppm by weight of Rh; P/Rh ratio:100) in a glass vessel with nitrogen blanketing. 500 g of toluene were transferred under nitrogen into the autoclave and a pressure of 27 MPa was then established by feeding synthesis gas, with stirring. After a reaction temperature of 130° C. was achieved, preforming was carried out for two hours. 500 g of dicyclopentadiene were then pumped into the autoclave over the course of 1 hour. By cooling with an air fan, the temperature of 130° C. was maintained. After the completion of dicyclopentadiene feed, the mixture was allowed to react further for 3 hours more. The pH in this case was in the range of 3.5 to 4.3. The autoclave was then cooled to room temperature and depressurized. The autoclave contents were then transferred by the residual pressure into a 2 liter three-neck flask equipped with an immersion branch stub and weighed. The dicyclopentadiene conversion rate given in each case in Table 1 was calculated from the increase in weight.

The hydroformylation of the dicyclopentadiene using the ammonium salts of TPPTS according to Examples 2–7 and the Comparison Experiment 1 was performed in a similar manner. The results obtained are summarized in Table 1.

c) Single-stage membrane filtration

The particular above reaction product from b) was applied to a laboratory membrane filter unit and the membrane used was a polyaramid membrane from Hoechst AG (UF-PA (PET 100)). The membrane was first heated for 10 minutes at 80° C. in water and the membrane was then overflowed with 200 l/h using a circulation pump and a pressure of 1 MPa was established. At an operation temperature of 40° C., the amount of hydroformylation product reported in Table 1 passed through the membrane as permeate. The content of catalyst constituents was determined in the permeate, from which the retention values reported in Table 1 were obtained, based on the hydroformylation reaction mixture used.

Examples 8 and 9. Comparison Experiment 2

Continuous hydroformylation of dicyclopentadiene (Examples 8 and 9: Use of distearylammonium salt of TPPTS as ligand in the rhodium catalyst system; Comparison Experiment 2: Use of methyl distearylammonium salt of TPPTS as ligand in the rhodium catalyst system)

The hydroformylation was performed continuously in a 17 liter pressurized tube under the reaction conditions specified in Table 2. When the methyl distearylammonium salt of TPPTS was used (Comparison Experiment 2), the influence of a low P/Rh ratio of 15 became noticeable. It was found that a rhodium loss of 15% occurred over the course of the hydroformylation. On changing over to a higher P/Rh ratio, Rh losses in the hydroformylation were no longer observed (Example 8).

The product continuously arising from Example 9 was cooled to 40° C. after the hydroformylation, stored temporarily in exchangeable reservoirs blanketed with nitrogen and then subjected to membrane filtration. To obtain a high retention of ligand and Rh complex compound, the membrane filtration was carried out in two stages here. The membrane unit comprised Standard Plate Modules from Dow (type DDS 30-4.5). The membrane area of the 1st stage was 1.4 m$^2$ and that of the second stage was 0.2 m$^2$. The filtration was carried out at an operating temperature of 40° C. Within the module, the reaction mixture to be filtered was conducted in each case along the membrane surface. The overflow was 0.5–2.5 m/sec. The hydroformylation reaction mixture was diluted with toluene prior to the 1st filtration stage to such an extent that the toluene content was 50–55% by weight. The reaction mixture was then concentrated in the 1st filtration stage to 50%, based on the total amount used.

The permeate obtained downstream of the 1st filtration stage, after supplementing small amounts of rhodium and DSA/TPPTS in accordance with the Rh and P(III) losses listed in Table 2, was fed to the 2nd filtration stage. The retentates of the two stages were combined and recycled directly back to the hydroformylation reaction. The hydroformylation reaction product, tricyclodecanedialdehyde, and thick oil which was also formed, permeated the membrane, in addition to the toluene under the prevailing operating pressure of 1 MPa in each case in the 1st and 2nd stages and were delivered for further workup as permeate. For this purpose, the toluene was first distilled off from the permeate and recycled to the hydroformylation reaction mixture upstream of the membrane filtration, the hydroformylation reaction mixture being diluted to 50% by weight.

The flow rates shown in Table 3 were determined for the two filtration stages of Example 9. During the continuous experimental period of over 12 weeks, no reduction in activity was observed. The majority of the P(III) losses were due to phosphine oxide formation.

Influence of pressure conditioning of the polyaramid membrane on the separation efficiency An unheated UF-PA 5 (PET 100) membrane was installed into a laboratory cell and then impinged with the hydroformylation reaction mixture from Example 9. The permeate and retentate obtained under the membrane filtration conditions of Example 9 (see Table 2) were recombined downstream of the membrane filtration and recycled to the hydroformylation reaction mixture upstream of the membrane filtration. The retention values for phosphorus(III) were analyzed as a function of time (see Table 3).

TABLE 3

| Pressure conditioning time [h] | 6 | 16 | 32 | 34 | 37 |
|---|---|---|---|---|---|
| P(III) retention; [% of that used] | 65 | 71 | >90 | >90 | >90 |

Examples 10–13

Continuous hydroformylation of dicyclopentadiene with variation of the rhodium concentration, based on DCP.

The hydroformylation was performed continuously under the reaction conditions specified in Table 4. The subsequent membrane filtration was carried out in a similar manner to Example 9. The results obtained are summarized in Table 4. It can be seen that activity and selectivity increase with increasing rhodium concentration and the membrane filtration results improved simultaneously.

Examples 14–17

Membrane filtration of a reaction mixture of the continuous hydroformylation of DCP, using the distearylammonium salt of TPPTS as ligand in the Rh catalyst system.

In Examples 14–17, the relationship between the toluene concentration in the reaction mixture used for the membrane filtration and the flow rate, and also the retention rates was studied. For the membrane filtration, a reaction mixture was used which was obtained by continuous hydroformylation under the conditions specified in Example 8 and at a phosphorus:rhodium ratio of 76.

The membrane filtration was carried out in a single stage at an operating temperature of 40° C., a pressure of 1 MPa and an overflow of 200 l/h over the membrane. The resulting flow rates and retention values are summarized in Table 5. It can be seen that an increase in the proportion of toluene in the reaction mixture used for the membrane filtration had a beneficial effect, both on the flow rates and on the retention rates.

TABLE 1

Batchwise hydroformylation of dicyclopentadiene and single-stage membrane filtration of the hydroformylation reaction mixture, using different ammonium salts of TPPTS as ligands

| | | Hydroformylation | | | Membrane filtration | | | |
| | | | | | | Retention | | |
| | | | Selectivity | Amount of permeate | | [% of initial amount] | | |
| Example | Amine of the TPPTS ammonium salt | Conversion rate [%] | dealdehyde/ monoenal | [% of initial amount] | Flow rate [l/m$^2$/h] | Rh | Ligand [P] | Amine [N] |
|---|---|---|---|---|---|---|---|---|
| W1 | Triisooctylamine | 99.9 | 99/1 | 15 | 64 | 89.3 | 69.8 | 16.5 |
| 1 | Methylditallowamine | 99.6 | 92/8 | 11 | 71 | 91.9 | 95.0 | 76.4 |
| 2 | Distearylamine | 99.4 | 97/3 | 66 | 61 | 97.5 | 96.1 | 78.3 |
| 3 | Methyldistearylamine | 99.4 | 95/5 | 10 | 77 | 97.1 | 94.3 | |
| 4 | Triacetylamine | 98.7 | 96/4 | 22 | 44 | 95.0 | 90.0 | 73.3 |
| 5 | Tri-n-octadecylamine | 98.5 | 91/9 | 53 | 49 | 93.0 | 87.0 | 88.7 |
| 6 | Trisicosylamine | 99.0 | 95/5 | 22 | 59 | 98.9 | 95.9 | 88.3 |
| 7 | Tridocosylanine | 99.7 | 90/10 | 48.8 | 29 | 96.5 | 94.7 | 81.9 |

TABLE 2

Continuous hydroformylation of DCP

|  | VV2 | Example 8 | Example 9 |
|---|---|---|---|
| Amine | MDSA* | DSA | DSA |
| Rh concentration based on DCP [ppm by weight] | 157 | 100 | 100 |
| Pressure [MPa] | 27 | 27 | 27 |
| P(III)/Rh ratio [mol/mol] | 15 | 85 | 100 |
| Temperature [°C.] | 135 | 135 | 130 |
| Throughput: Volume of DCP/(reactor volume) · hour [l/h] | 0.07 | 0.07 | 0.03** |
| Toluene concentration, based on DCP in the hydroformylation [%] | 42 | 44 | <.15 |
| Conversion rate [%] | 100 | 100 | 100 |
| Dial/monoenal ratio | 89/11 | 89/11 | 91/9 |
| Rh losses [% of initial amount] | 15 | — | 0.8 |
| P(III) losses [% of initial amount] |  |  | 2 |
| Permeate flux |  |  |  |
| 1st stage [l/m²h] |  |  | 6 |
| 2nd stage [l/m²h] |  |  | 30 |

*Methyldistearylamine
**The throughput rate was adapted to the membrane unit available and reduced more intensively.

TABLE 4

|  | Example 9 | Example 10 | Example 11 | Example 12 |
|---|---|---|---|---|
| Amine | DSA | DSA | DSA | DSA |
| Rh concentration based on DCP [ppm by weight] | 100 | 60 | 45 | 20 |
| Pressure [MPa] | 27 | 27 | 27 | 27 |
| P(III)/Rh ratio [mol/mol] | 100 | 100 | 100 | 100 |
| Temperature °C.] | 130 | 130 | 130 | 130 |
| Throughput: Volume of DCP/(reactor volume) · hour [l/h] | 0.03** | 0.03** | 0.03** | 0.03** |
| Toluene concentration, based on DCP in the hydroformylation [%] | <15 | <15 | <15 | <15 |
| Conversion rate [%] | 100 | 100 | 100 | 100 |
| Dial/monoenal ratio | 91/9 | 60/40 | 40/60 | 27/73 |
| Membrane filtration pressure [MPa] | 1 | 1 | 1 | 1 |
| Rh losses [% of initial amount] | 0.8 | 1.4 | 1.7 | 2.0 |
| P(III) losses [% of initial amount] | 2 | 3.5 | 4.2 | 5.0 |
| Flow rate |  |  |  |  |
| 1st stage (l/m² h) | 6 | 6.5 | 7.1 | 7.6 |
| 2nd stage (l/m² h) | 30 | 33 | 37 | 41 |

**The throughput rate was adapted to the membrane unit available and reduced more intensively

TABLE 5

| Composition of the hydroformylation mixture used for the membrane filtration | | | Flow rate [l/m²h] based on | | Retention rates [% of initial amount] | | | |
|---|---|---|---|---|---|---|---|---|
| Aldehyde [%] based on the total of aldehydes and toluene | Toluene | | the total reaction mixture used for the membrane filtration | the aldehydes present in the reaction mixture | Rh | PIII | $P_{tot.}$ | $N_{tot.bas.}$ |
| 80 | 20 | | 7 | 5.6 | 97.3 | 92.4 | 94.9 | 75.7 |
| 70 | 30 | | 12 | 8.4 | 98.5 | 88.8 | 96.4 | 76.9 |
| 56 | 44 | | 20 | 11.2 | 98.8 | 93.2 | 97.0 | 76.3 |
| 34 | 66 | | 61 | 19.9 | 99.7 | 96.0 | 98.4 | 83.8 |

Various modifications of the process of the invention may be made without departing from the spirit or scope thereof and it is to be understood that the invention is intended to be limited only as defined in the appended claims.

What we claim is:

1. A process for preparing aldehydes comprising hydroformylating olefinically unsaturated compounds with hydrogen and carbon monoxide in a homogeneous phase in the presence of a catalyst system comprising rhodium complex compounds and aromatic phosphines in a molar excess and separating off the catalyst system from the hydroformylation reaction mixture by pressure filtration on a semipermeable membrane of an aromatic polyamide, the hydroformylation being effected at a pH of 2.5 to 4.3 using a molar ratio of phosphine:rhodium of at least 60 and at a rhodium concentration of at least 10 ppm by weight, based on the olefinically unsaturated compound used, and, using, as aromatic phosphines, alklyammonium and/or arylammonium salts of sulfonated or carboxylated triarylphosphines of the formula

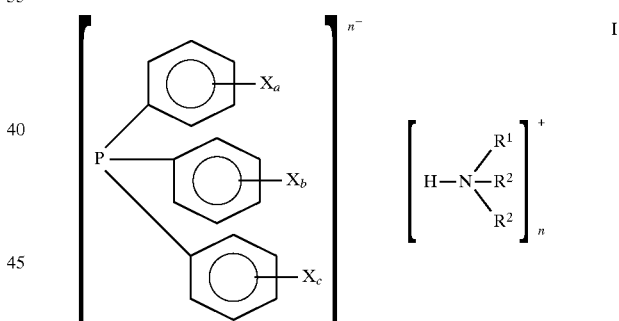

wherein X is sulfonate ($SO_3^-$) or carboxylate ($COO^-$), a, b and c are individually 0 or 1, wherein at least one of a, b, or c must be equal to 1, n is equal to 1, 2 or 3, $R^1$ and $R^2$ are individually selected from the group consisting of alkyl of 8 to 13 carbon atoms, $C_6$–$C_{10}$-aryl of 6 to 10 carbon atoms, cycloalkyl of 6 to 10 carbon atoms, and $R^1$ can also be hydrogen, and the total of the carbon atoms in $R^1$ and $R^2$ must be at least 30.

2. The process of claim 1, wherein X in formula I is sulfonate.

3. The process of claim 1, wherein $R^1$ and $R^2$ in formula I are individually selected from the group consisting of 12 to 22 carbon atoms or phenyl or cyclohexyl.

4. The process of claim 1, wherein a, b and c are equal to 1.

5. The process of claim 1, wherein the ammonium cations $[HNR^1R^2R^2]^+$ in formula I contain in total at least 30 carbon atoms in $R^1$ and $R^2$.

6. The process of claim 5, wherein the ammonium cations $[HNR^1R^2R^2]^+$ in formula I are selected from the group consisting of distearylammonium ion, tricetylammonium ion and tri-n-octadecylammonium ion.

7. The process of claim 1, wherein the molar ratio of rhodium to aromatic phosphine of formula I is 1:(60–120).

8. The process of claim 1, wherein the Rh concentration in the hydroformylation, based on the olefinically unsaturated compound, is at least 20 ppm by weight.

9. The process of claim 1, wherein the catalyst system is prepared in a step upstream of the process or is formed in situ during the process.

10. The process of claim 9, wherein, to prepare the catalyst system in an upstream step, the rhodium component and the diphosphine of formula I, each dissolved or suspended in an organic solvent, are brought together and reacted for at least 1 hour at a temperature of 80°–150° C. under a carbon monoxide/hydrogen pressure of 15–25 MPa.

11. The process of claim 1, wherein the olefinically unsaturated compounds used are selected from the group consisting of substituted or unsubstituted alkenes of 2 to 30 carbon atoms, substituted or unsubstituted dienes of 4 to 10 carbon atoms, substituted or unsubstituted cycloalkenes or dicycloalkenes of 5 to 12 carbon atoms in the ring system, esters of an unsaturated carboxylic acid of 3 to 20 carbon atoms and of an aliphatic alcohol of 1 to 18 carbon atoms, esters of a saturated carboxylic acid of 2 to 20 carbon atoms and of an unsaturated alcohol of 2 to 18 carbon atoms, unsaturated alcohols or ethers of 3 to 20 carbon atoms or araliphatic olefins of 8 to 20 carbon atoms.

12. The process of claim 11, wherein the olefinically unsaturated compound used is dicyclopentadiene.

13. The process of claim 1, wherein the hydroformylation is carried out at a temperature of 100°–140° C., and at a pressure of 0.5–27 MPa.

14. The process of claim 1, wherein the hydroformylation is carried out at a pH of 3.0–4.0.

15. The process of claim 1, wherein it is carried out in the presence of an organic solvent.

16. The process of claim 15, wherein the solvent concentration in the hydroformylation reaction is 5–25% by weight, based on the total hydroformylation reaction mixture, and in the membrane filtration is 30–70% by weight, based on the total reaction mixture used for the membrane filtration.

17. The process of claim 1, wherein, in the hydroformylation reaction mixture used for the membrane filtration, the concentration of the aromatic phosphines of the formula I present in excess is 2.5–25% by weight, based on the total reaction mixture used for the membrane filtration.

18. The process of claim 1, wherein the concentration of the rhodium complex compounds in the hydroformylation reaction mixture used for the membrane filtration is 2–400 ppm by weight, based on the total reaction mixture used for the membrane filtration.

19. The process of claim 1, wherein the membrane filtration is performed at a pressure of 0.1–15 MPa and is carried out as a single-stage or multistage process.

20. The process of claim 1, wherein the membrane filtration is carried with series-connected separation stages.

21. The process of claim 1, wherein the amount of retentate of the membrane filtration is 8–90%, based on the reaction mixture used for the membrane filtration, and the concentration of the separated aromatic phosphines of formula I in the retentate is at least three times as high as that in the hydroformylation mixture used for the membrane filtration.

22. The process of claim 1, wherein, in the two-stage membrane filtration, the ratio of the amount of retentate of the 1st filtration stage to the amount of retentate of the 2nd stage is about 1:1.

23. The process of claim 1, wherein the retentates of the membrane filtration separation stages which contain the catalyst system are recycled to the hydroformylation, optionally with supplementary addition of the rhodium and/or the rhodium complex compounds and of the aromatic phosphines of formula I.

24. The process of claim 23, wherein, in the case of the two-stage membrane filtration procedure, the supplementary addition of the rhodium and/or of the rhodium complex compounds and of the aromatic phosphines of formula I is made in advance to the permeate of the 1st filtration stage prior to its feed to the 2nd filtration stage.

25. The process of claim 1, wherein the solvent is separated by distillation from the combined permeates of the membrane separation stages, recycled upstream of the membrane filtration and added to the hydroformylation reaction mixture upstream of the membrane filtration.

* * * * *